United States Patent
Hu

(12) 
(10) Patent No.: US 6,478,779 B1
(45) Date of Patent: Nov. 12, 2002

(54) ASSEMBLY OF NEEDLE HOLDER AND BARREL OF SAFETY SYRINGE

(75) Inventor: Chien-Kung Hu, Miao Li Hsien (TW)

(73) Assignees: Li-Hua Lu, Miao Li Hsien (TW); Hung-Yang Fan, Miao Li Hsien (TW); Chu-Chun Chiu, Miao Li Hsien (TW)

( * ) Notice: Subject to any disclaimer, the term of this patent is extended or adjusted under 35 U.S.C. 154(b) by 0 days.

(21) Appl. No.: 09/887,178

(22) Filed: Jun. 25, 2001

(51) Int. Cl.[7] ................................................ A61M 5/00
(52) U.S. Cl. ........................ 604/187; 604/196; 604/210; 604/228
(58) Field of Search .................... 604/181, 186–188, 604/192, 195, 198, 220, 228, 240–242, 243

(56) References Cited

U.S. PATENT DOCUMENTS 5,785,687 A * 7/1998 Saito ........................... 604/110
6,206,859 B1 * 3/2001 Niedospial, Jr. et al. .... 604/220

* cited by examiner

Primary Examiner—David J. Walczak
Assistant Examiner—Anuradha Ramana
(74) Attorney, Agent, or Firm—Browdy and Neimark

(57) ABSTRACT

A safety syringe comprises a barrel having a retaining block disposed in the receiving hole, an initial stop portion and a final stop portion disposed in the end edge thereof, and a rotation resisting portion; a needle holder disposed in the barrel, and having a retaining groove and communicating with a port, a rotation stopping rod corresponding between the initial stop portion and the final stop portion of the barrel, overcoming portion capable of passing the rotation resisting portion of the barrel; and a plunger capable of catching and turning the needle holder. As the plunger is not engaged with the needle holder, the retaining groove of the needle holder confines the retaining block of the barrel. When the plunger is engaged with the needle holder which is turned, the overcoming portion of the needle holder overcomes the rotation resisting portion of the barrel, thereby enabling the port of the needle holder to be opposite in location to the retaining block of the barrel, so as to enable the needle holder to be drawn backwards.

10 Claims, 11 Drawing Sheets

ASSEMBLY OF NEEDLE HOLDER AND BARREL OF SAFETY SYRINGE

FIELD OF THE INVENTION

The present invention relates generally to a safety syringe, and more particularly to an improved assembly of needle holder and barrel of the safety syringe.

BACKGROUND OF THE INVENTION

The conventional safety syringe comprises a barrel and a needle holder which can be drawn into the barrel in the wake of injection, thanks to an engagement structure which is disposed between the barrel and the needle holder. However, the assembly of the barrel and the needle holder of the conventional safety syringe is defective in design in that the needle holder can be drawn into the barrel with a minimum effort, thereby resulting in user's inconvenience as well as injection hazard.

SUMMARY OF THE INVENTION

It is the primary objective of the present invention to provide a syringe comprising a barrel and a needle holder which can be restrictively rotated within a range by a predetermined rotational force, so as to enhance the safety of the syringe.

It is another objective of the present invention to provide a syringe with an assembling structure for joining the barrel and the needle holder of the syringe without difficulty.

In keeping with the principle of the present invention, the foregoing objectives of the present invention are attained by a safety syringe comprising a barrel, a needle holder, and a plunger. The barrel has a receiving hole, a retaining block located in the inner edge of the receiving hole, an initial stop portion, a final stop portion, and a rotation resisting portion. The needle holder has a retaining groove, a stop rotation rod capable of turning between the initial stop portion and the final stop portion of the barrel, a overcoming portion capable of passing the rotation resisting portion at the time when the needle holder is turned by a predetermined force, and a catching turning cooperating portion located at the rear end. The plunger has a front rod body received in the receiving hole of the barrel, a catching turning portion disposed at the front end for retaining the catching turning cooperating portion of the needle holder.

When the plunger is not yet engaged with the needle holder, the overcoming portion of the needle holder is stopped at the rotation resisting portion of the barrel. As the plunger is engaged with the needle holder such that the needle holder is turned, the overcoming portion of the needle holder overcomes the rotation resisting portion of the barrel, thereby enabling the retaining groove of the needle holder to be opposite in location to the retaining block of the barrel. The needle holder can be thus drawn back in.

DETAILED DESCRIPTION OF THE INVENTION

Figure 1:
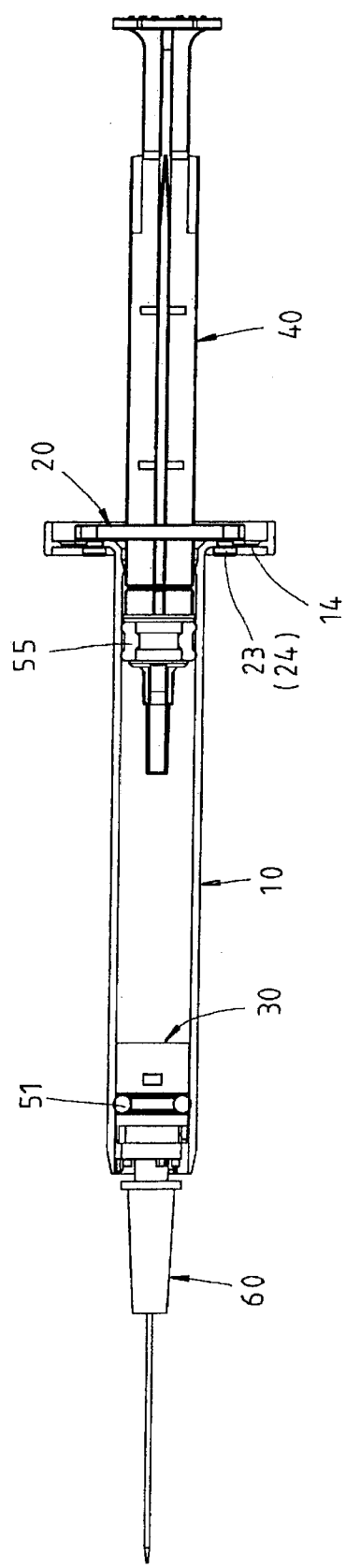
FIG. 1 is a top sectional view of a preferred embodiment of the present invention to show that the plunger and the needle holder are separated from each other.
Figure 2:
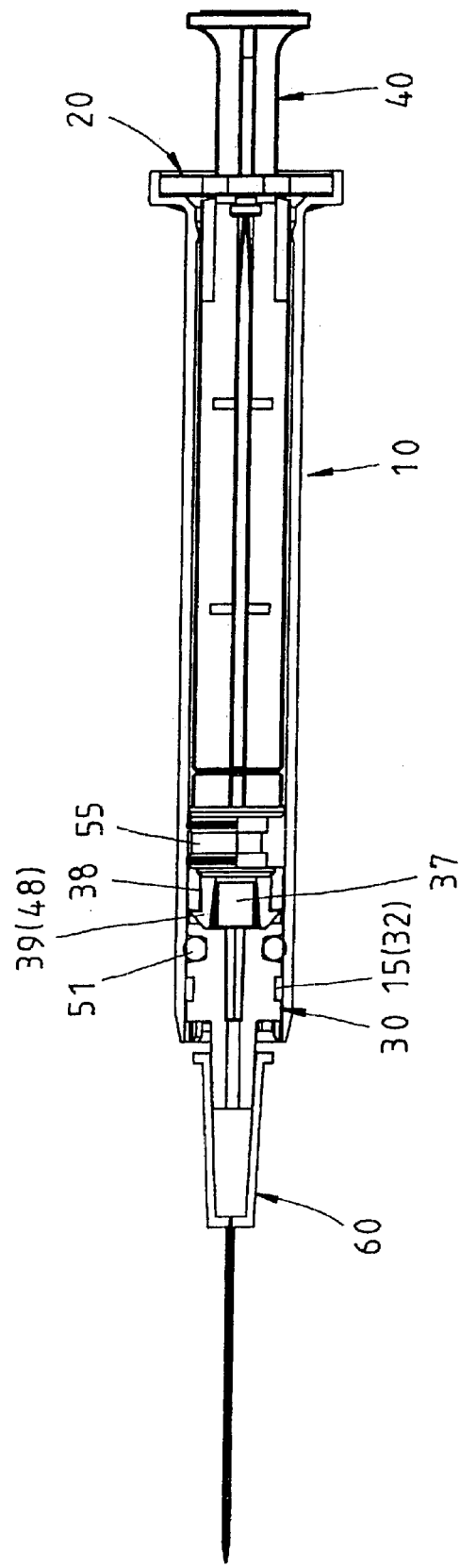
FIG. 2 is a front sectional view of the preferred embodiment of the present invention to show that the plunger is engaged with the needle holder.
Figure 3:
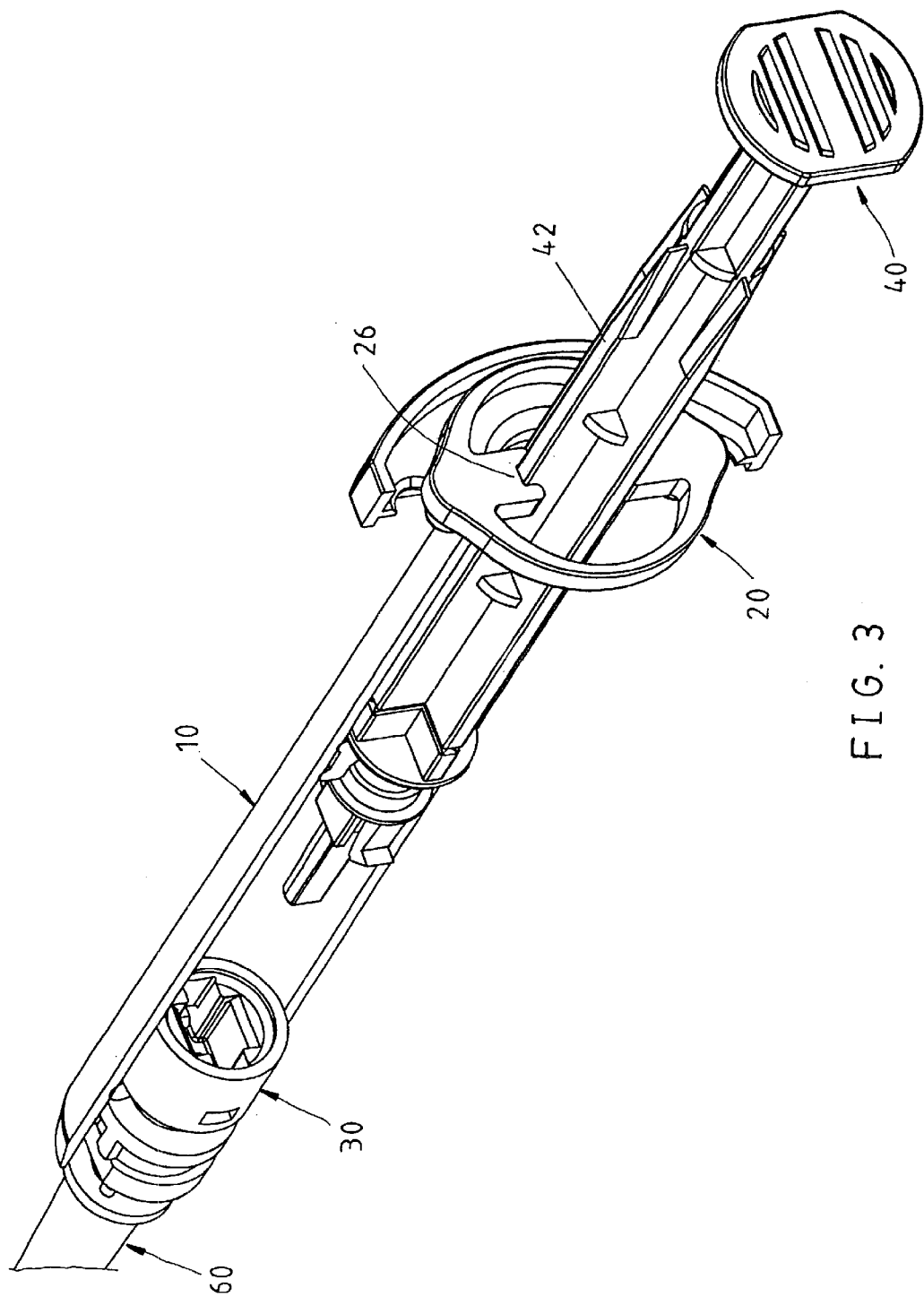
FIG. 3 shows a sectional view of the preferred embodiment of the present invention in combination.
Figure 4:
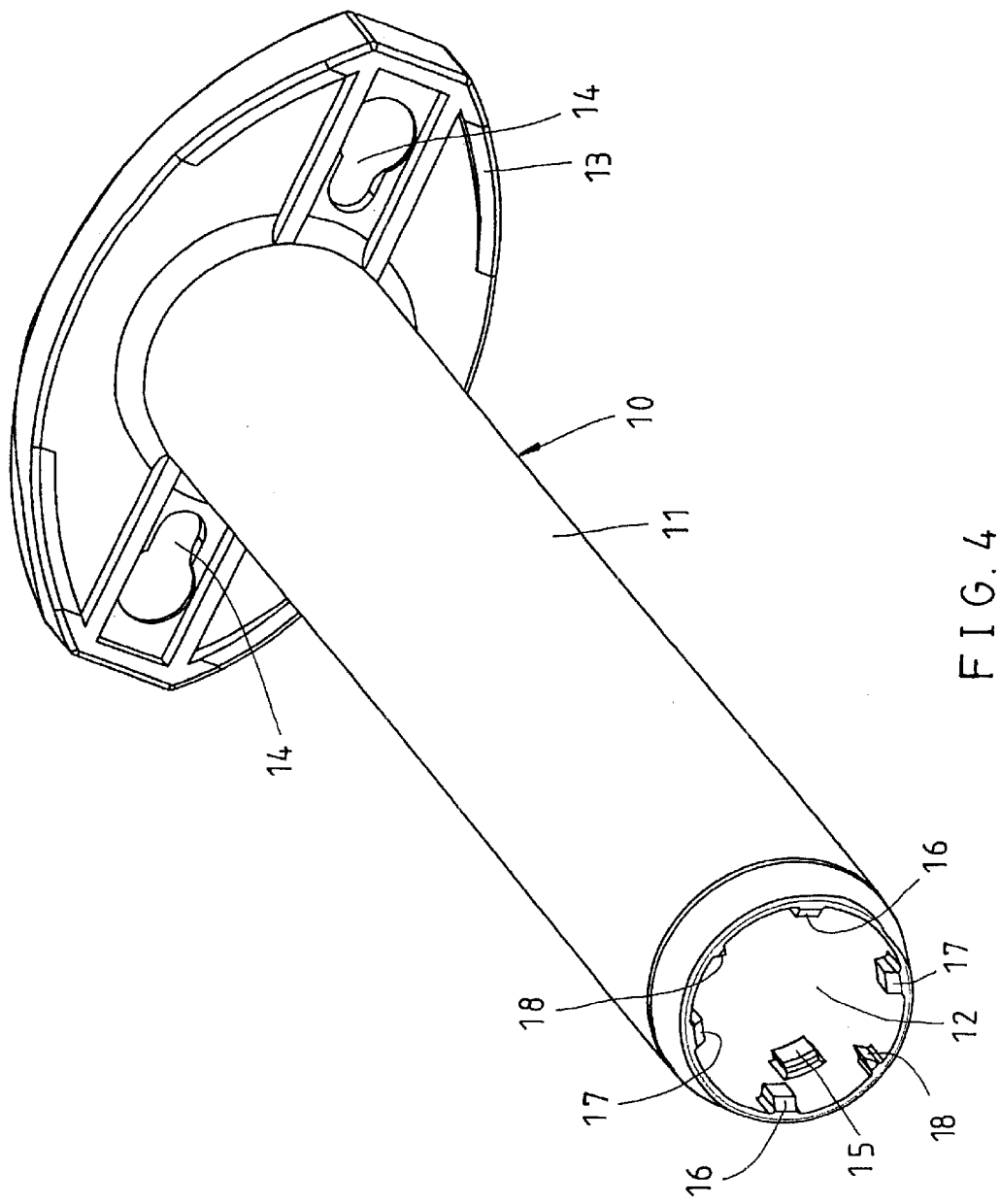
FIG. 4 is an enlarged view of the present invention to show the structure that retains the needle holder.
Figure 5:
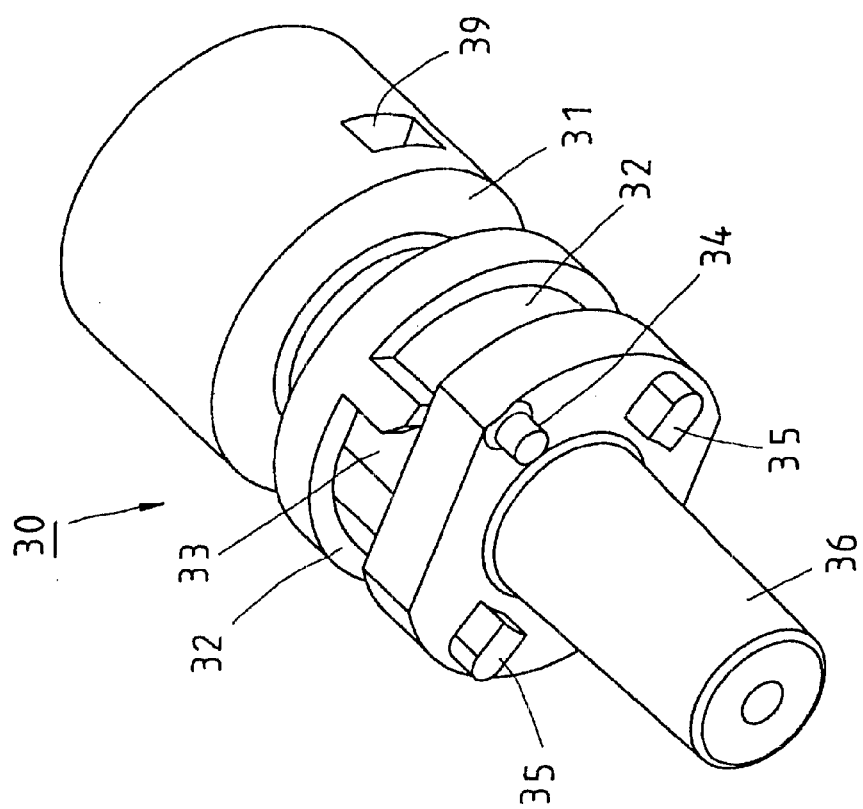
FIG. 5 shows a perspective view of the needle holder of the preferred embodiment of the present invention.
Figure 6:
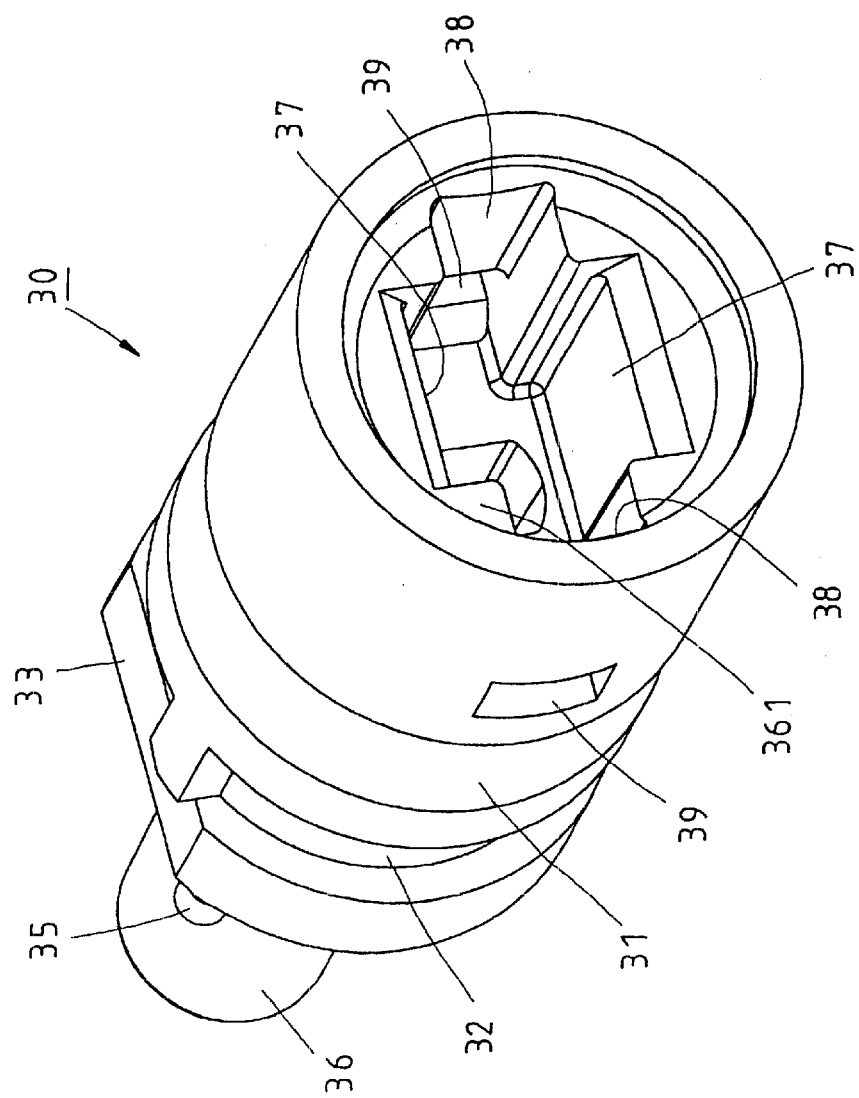
FIG. 6 shows another perspective view of the needle holder of the preferred embodiment of the present invention.
Figure 7:
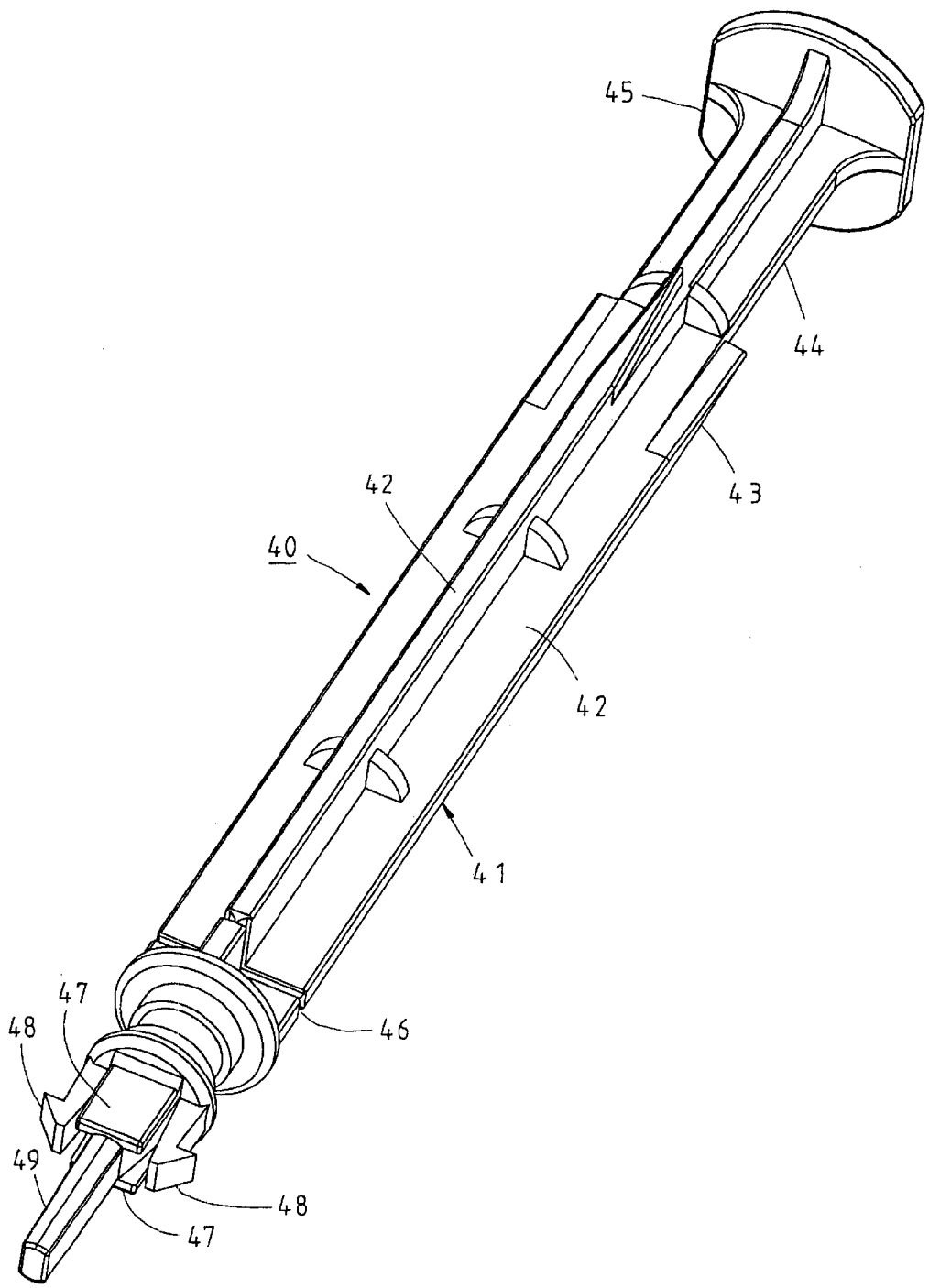
FIG. 7 shows a perspective view of the plunger of the preferred embodiment of the present invention.

As shown in FIGS. 1–3, a safety syringe embodied in the present invention is provided with a needle set 60.

As shown in FIGS. 3–7, the safety syringe of the preferred embodiment of the present invention comprises the following component parts.

A barrel 10 has a cylindrical body 11 which is provided with a receiving hole 12, a grip lug 13 disposed at rear end of the cylindrical body 11 and provided with two fitting holes 14, two retaining blocks 15 located oppositely in the inner edge of the receiving hole 12, two initial stop portions 16, two final stop portions 17, and two rotation resisting portions 18 disposed outside the initial stop portions 16 and the final stop portions 17.

As elastic lashing member 20 is disposed at the grip lug 13 of the barrel 10 and is provided with two locating pillars 23 which are in turn provided at the top end with an arresting head 24. The arresting heads 24 are retained in the fitting holes 14 of the barrel 10. Two slide confining slots 26 are disposed in the inner edges of two sides of the lashing member 20.

A needle holder 30 is assembled with the receiving hole 12 of the barrel 10 and is provided with a circular groove 31, an O-ring 51 received in the circular groove 31, two retaining grooves 32 located in the outer circumference thereof and provided at the front end with a port 33, two rotation stopping rods 34 corresponding in location between the initial stop portions 16 and the final stop portions 17, two overcoming portions 35 capable of passing the rotation resisting portion 18 of the barrel 10 at the time when the needle holder 30 is turned, a needle connection portion 36 provided with an insertion hole 361, and a catching turning cooperation portion which is an inner hole forming two rotational sides 37, two slide channels 38, and two catching holes 39 in communication with the slide channels 38.

A plunger 40 has a front rod body 41 received in the receiving hole 12 of the barrel 10, four slide pieces 42 provided at the end thereof with a pointed insertion plate 43, a rear rod body 44 connected with the rear segment of the front rod body 41, a press head 45 disposed at the rear rod body 44, a breaking portion 46, and a catching turning portion which is provided with two turning sides 47, two claws 48 disposed at the front end thereof and provided in opposite inner sides with a space for allowing an elastic deformation, and an insertion rod 49.

A stopper 55 is disposed at the front end of the plunger 40.

Figure 8:
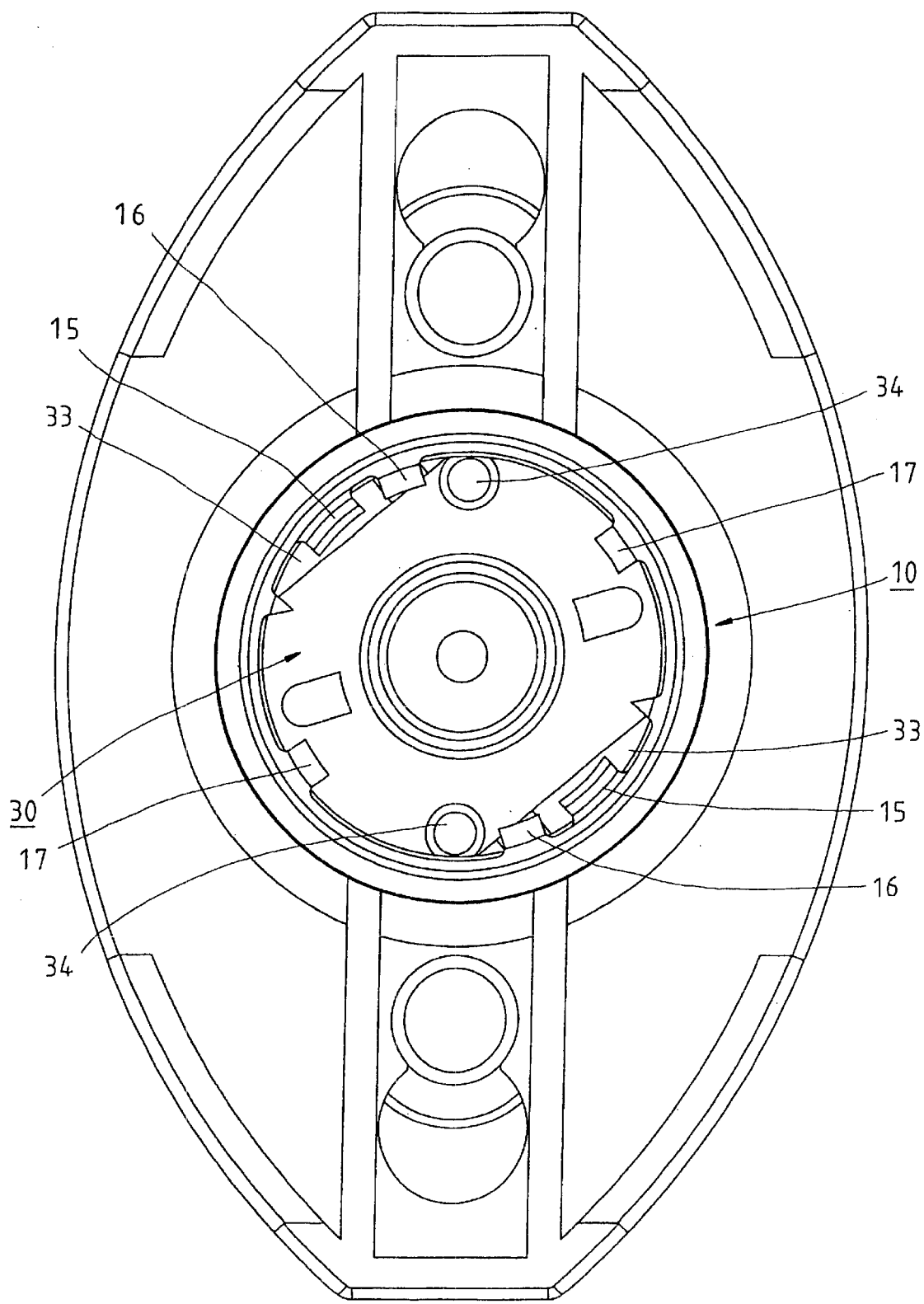
FIG. 8 is an end view of the preferred embodiment of the present invention to show that the needle holder can be removed forward and backward.

As shown in FIG. 8, the needle holder 30 is first joined with the barrel 10 such that the port 33 of the needle holder 30 is aligned with the retaining block 15 of the barrel 10, and that the rotation stopping rods 34 are located between the initial stop portions 16 and the final stop portions 17 of the barrel 10, and further that the needle holder 30 can be turned in relation to the barrel 10 within an angular range, which is 45 degrees.

Figure 9:
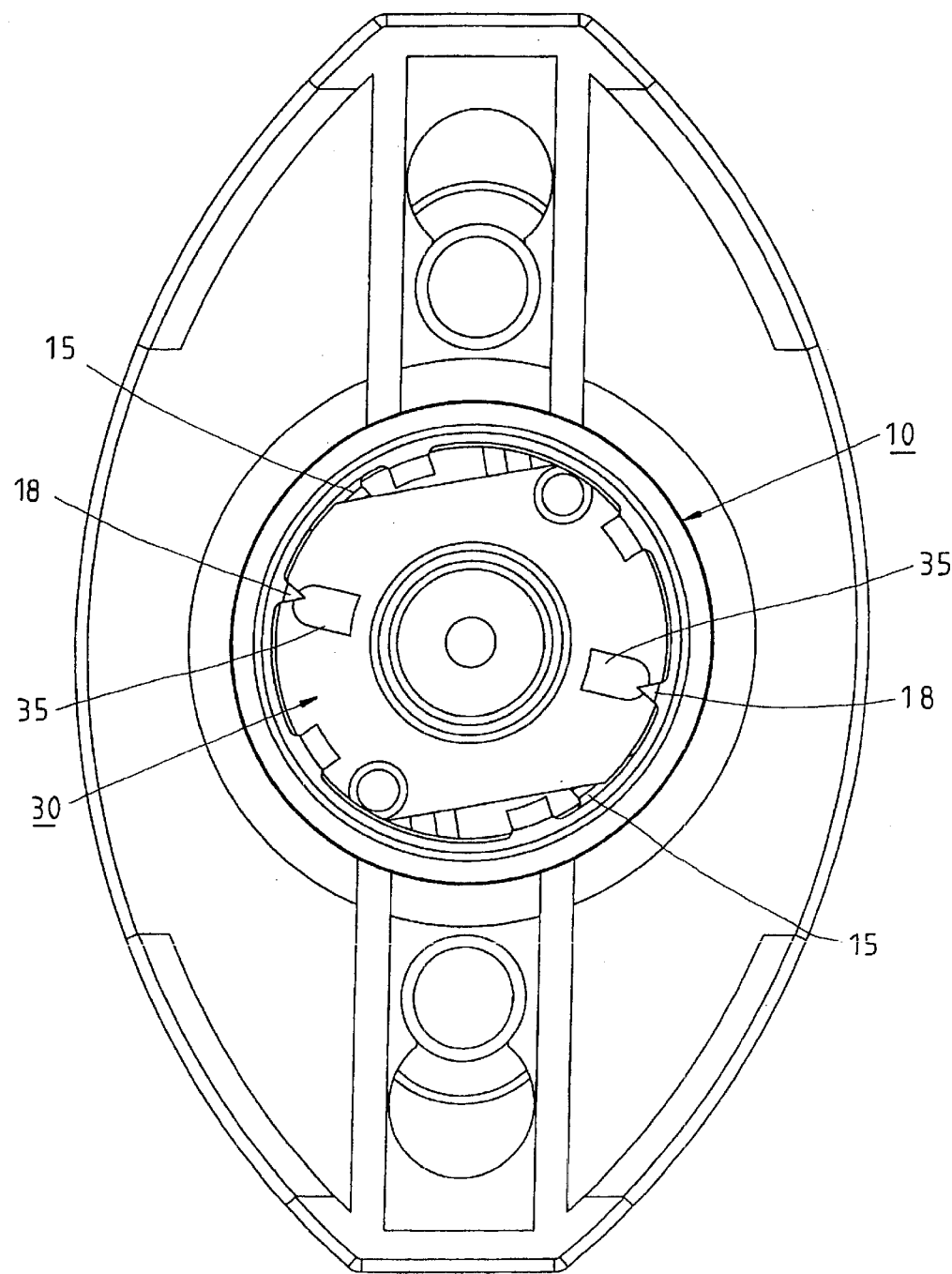
FIG. 9 is an end view of the preferred embodiment of the present invention to show that the overcoming portion of the needle holder passes the rotation resisting portion of the barrel.

As shown in FIG. 9, the needle holder 30 is then turned with a tool such that the overcoming portion 35 of the needle holder 30 is deformed to pass the rotation resisting portion 18 of the barrel 10, thereby enabling the retaining block 15 of the barrel 10 to be confined in the retaining groove 32 of the needle holder 30.

Figure 10:
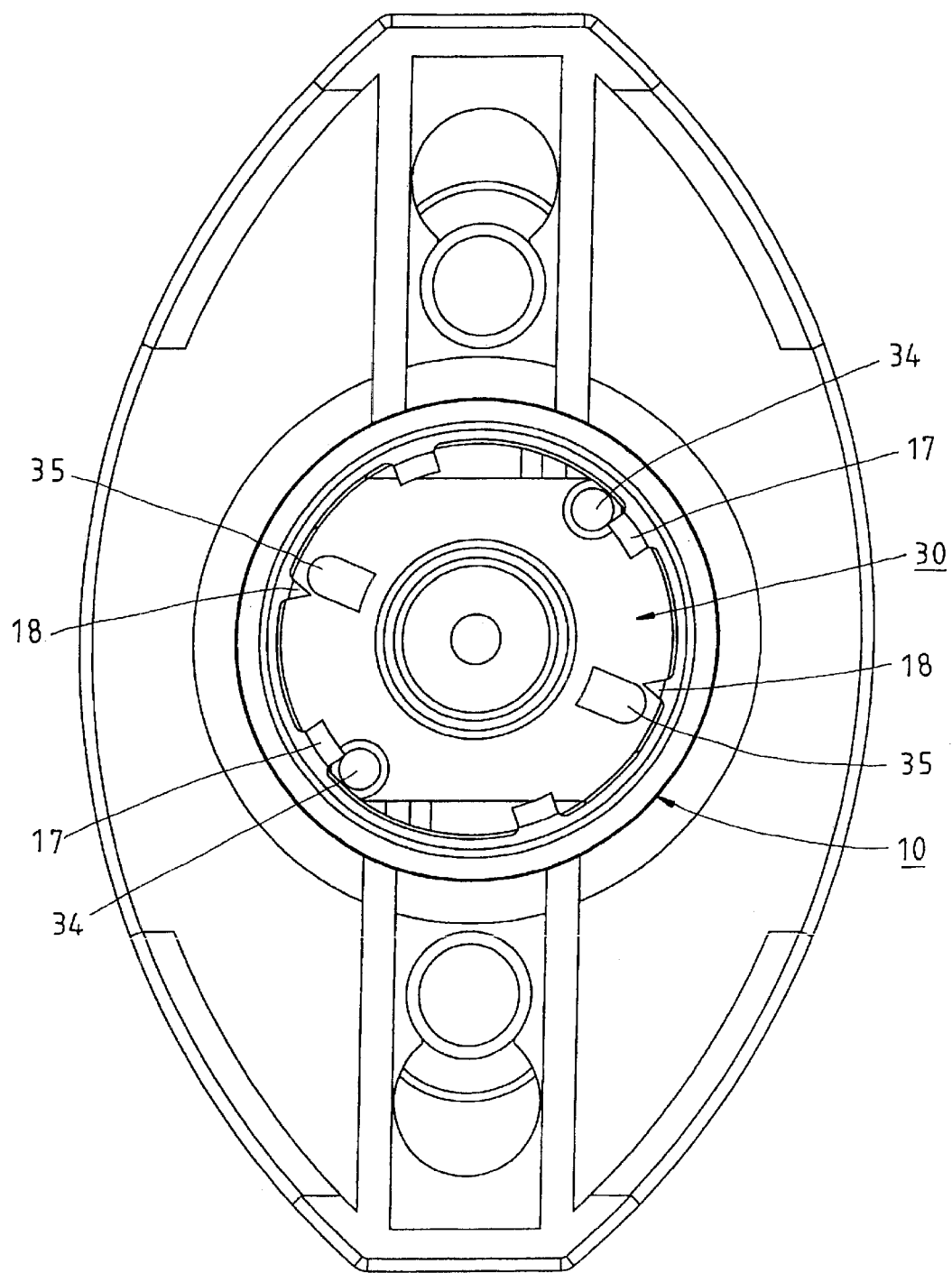
FIG. 10 is an end view of the preferred embodiment of the present invention to show that the needle holder can not be removed and displaced.

As shown in FIG. 10, the assembly of the preferred embodiment of the present invention is completed such that the needle holder 30 can not be caused by a force to displace axially, and that the needle holder 30 can not be drawn into the barrel 10 by accident.

The initial stage of operation of the present invention is shown in FIG. 1, in which two slide pieces 42 of the plunger 40 are shown being confined in the slide confining slots 26 of the elastic lashing member 20. As a result, the plunger 40 can not be turned in relation to the barrel 10.

As shown in FIG. 2, in the wake of injection, the plunger 40 is so located that the claws 48 are elastically deformed to slide into the slide channels 38 of the needle holder 30. In the meantime, the turning sides 47 of the plunger 40 come in contact with the rotational sides 37 of the needle holder 30. Finally, the claws 48 are engaged with the catching holes 39 of the needle holder 30. In addition, the rear rod body 44 of the plunger 40 is opposite in location to the elastic lashing member 20 and is not confined by the slide confining slot 26, so as to be capable of turning in relation to the barrel. The needle holder 30 can be thus turned by the plunger 40.

As illustrated in FIG. 9, the plunger 40 is exerted on by a greater rotational force $T_2$ to overcome the rotation resisting portion 18 of the barrel 10, thereby enabling the plunger 40 to turn.

As shown in FIG. 8, the needle holder 30 is so turned that the needle holder 30 can be separated from the barrel 10. The two ports 33 of the needle holder 30 are respectively corresponding to the retaining blocks 15 of the barrel 10. The needle holder 30 can be drawn into the receiving hole 12 of the barrel 10 by the plunger 40.

Figure 11:
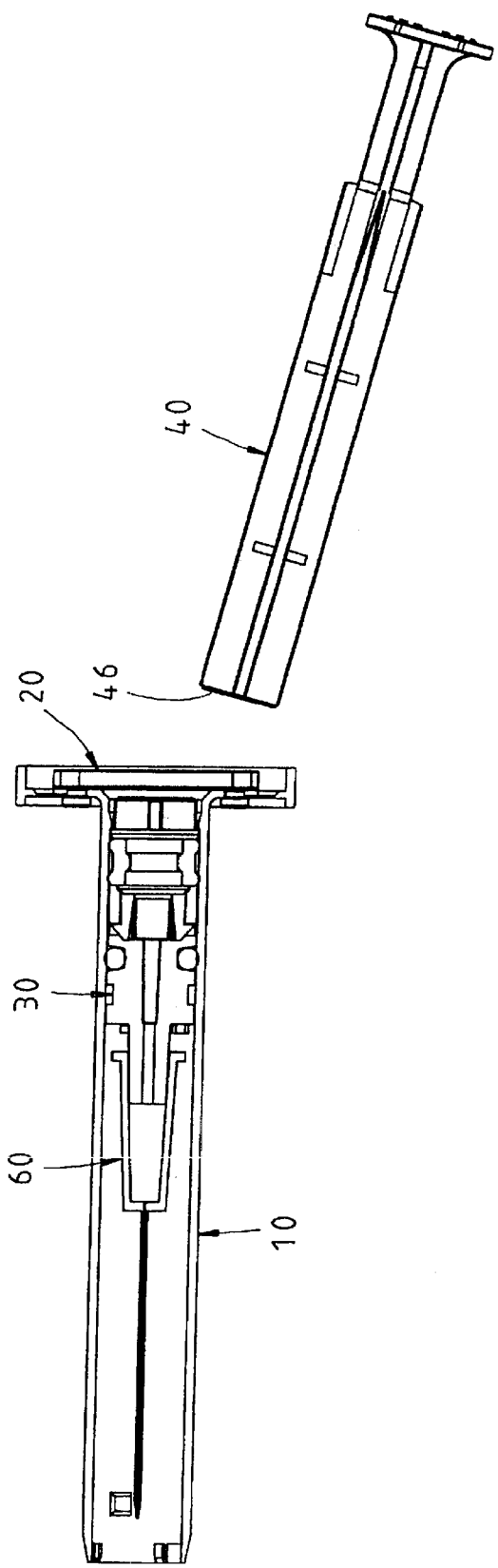
FIG. 11 is a top sectional view of the preferred embodiment of the present invention to show that the needle holder is drawn back in and that the plunger is broken.

As shown in FIG. 11, the needle holder 30 and the needle set 60 are drawn into the interior of the barrel 10 by the plunger 40, which is then broken at the breaking portion 46 thereof, so as to prevent the needle set 60 from being pushed out.

It is therefore apparent that the preferred embodiment of the present invention has advantages over the prior art. In the first place, the barrel of the safety syringe of the present invention is so structured to confine the rotational range of the needle holder. The needle holder can be turned only by a force of a predetermined magnitude, thereby enhancing the safety of the syringe of the present invention. In addition, the syringe of the present invention is provided with the assembly structure which is simple in construction and operation, and is effective in confining the needle holder.

What is claimed is:

1. A safety syringe provided with a needle set attached thereto, said safety syringe comprising:

a barrel having a cylindrical body which is provided with a receiving hole, a retaining block disposed in an inner edge of said receiving hole, an initial stop portion, a final stop portion, and a rotation resisting portion disposed outside of said initial stop portion and said final stop portion;

a needle holder having in an outer circumference thereof a retaining groove which is provided at a front end with a port, a rotation stopping rod confined between said initial stop portion and said final stop portion of said barrel to confine the rotation of said needle holder, an overcoming portion capable of passing said rotation resisting portion of said barrel at such time when said needle holder is turned by a predetermined rotational force, a catching turning cooperating portion located at the rear end thereof, and a needle connection portion;

a plunger having a front rod body received in said receiving hole of said barrel, a catching turning portion located at the front end thereof to retain said catching turning cooperating portion of said needle holder;

said rotation stopping rod of said needle holder being confined by said initial stop portion and said final stop portion of said barrel so as to turn only a predetermined angle, said overcoming portion of said needle holder being stopped at said rotation resisting portion of said barrel at the time when said plunger is not engaged with said needle holder, said overcoming portion of said needle holder capable of overcoming said rotation resisting portion to enable said port of said needle holder to be opposite in location to said retaining block of said barrel at the time when said plunger is engaged with said needle holder, thereby enabling said needle holder to be drawn into said barrel by said plunger.

2. The safety syringe as defined in claim 1 further comprising an elastic lashing member which is disposed in a rear end of said barrel and is provided in the inner side of two ends thereof with a slide confining slot; wherein said plunger is provided with two slide pieces corresponding to said two slide confining slots of said elastic lashing member.

3. The safety syringe as defined in claim 1, wherein said initial stop portion and said final stop portion of said barrel confines said needle holder to rotate in an angle of 45 degrees.

4. The safety syringe as defined in claim 1, wherein said barrel has two retaining blocks, two initial stop portions, two final stop portions, and two rotation resisting portions; wherein said needle holder has two retaining grooves, two ports, two rotation stopping rods, and two overcoming portions.

5. The safety syringe as defined in claim 1, wherein said catching turning cooperating portion of said needle holder is provided with two slide channels and two catching holes; wherein said catching turning portion of said plunger is provided with a claw which slides into said slide channel of said needle holder to engage said catching hole.

6. The safety syringe as defined in claim 1, wherein said needle holder is provided further inwards with an insertion hole; wherein said catching turning portion of said plunger is provided further forward with an insertion rod which is inserted into said insertion hole of said needle holder.

7. The safety syringe as defined in claim 1, wherein said plunger is provided with four slide pieces.

8. The safety syringe as defined in claim 1, wherein said catching turning cooperating portion of said needle holder is provided with two rotational sides; wherein said catching turning portion of said plunger is provided with two turning sides for driving said rotational sides of said needle holder, thereby causing said needle holder to turn.

9. The safety syringe as defined in claim 1, wherein said needle holder further has a circular groove, and an O-ring received in said circular groove for sealing off said receiving hole of said barrel.

10. The safety syringe as defined in claim 1, wherein said plunger is provided at the front end with a stopper for scaling off said receiving hole of said barrel.

* * * * *